(12) United States Patent
Thalhammer et al.

(10) Patent No.: US 9,402,548 B2
(45) Date of Patent: Aug. 2, 2016

(54) RADIATION DETECTOR AND MEASUREMENT DEVICE FOR DETECTING X-RAY RADIATION

(75) Inventors: Stefan Thalhammer, Munich (DE); Markus Hofstetter, Neubiberg (DE); John Howgate, Munich (DE); Martin Stutzmann, Erding (DE)

(73) Assignee: Stefan Thalhammer, Munich (DE)

( * ) Notice: Subject to any disclaimer, the term of this patent is extended or adjusted under 35 U.S.C. 154(b) by 93 days.

(21) Appl. No.: 14/003,082

(22) PCT Filed: Mar. 2, 2012

(86) PCT No.: PCT/EP2012/000945
§ 371 (c)(1),
(2), (4) Date: Dec. 12, 2013

(87) PCT Pub. No.: WO2012/119740
PCT Pub. Date: Sep. 13, 2012

(65) Prior Publication Data
US 2014/0093038 A1    Apr. 3, 2014

(30) Foreign Application Priority Data

Mar. 4, 2011    (DE) .......................... 10 2011 013 057

(51) Int. Cl.
| | |
|---|---|
| *H04N 5/32* | (2006.01) |
| *A61B 5/00* | (2006.01) |
| *G01T 1/24* | (2006.01) |
| *H01L 31/08* | (2006.01) |
| *H01L 31/103* | (2006.01) |

(52) U.S. Cl.
CPC ................. *A61B 5/0093* (2013.01); *G01T 1/24* (2013.01); *H01L 31/085* (2013.01); *H01L 31/1035* (2013.01); *H04N 5/32* (2013.01)

(58) Field of Classification Search
CPC ....................................................... H04N 5/32
See application file for complete search history.

(56) References Cited

U.S. PATENT DOCUMENTS 3,265,899 A * 8/1966 Bergstrom ................ G01J 1/42
                                                      257/458
5,677,538 A * 10/1997 Moustakas et al. ....... 250/370.12
5,742,659 A    4/1998 Atac et al.
(Continued)

FOREIGN PATENT DOCUMENTS

| EP | 1376155 A1 | 1/2004 |
| EP | 2194403 A1 | 6/2010 |

(Continued)

OTHER PUBLICATIONS

Hofstetter et al., Development and evaluation of gallium nitride-based thin films for x-ray dosimetry, May 4, 2011, Physics in Medicine and Biology, vol. 56, pp. 3215-3231.*

(Continued)

*Primary Examiner* — Christine Sung
(74) *Attorney, Agent, or Firm* — Caesar Rivise, PC

(57) ABSTRACT

The invention relates to a radiation detector (10), in particular for detecting x-ray radiation, comprising a carrier substrate (11), a detector layer (12) which comprises GaN, is arranged on the carrier substrate (11) and has a thickness less than 50 μm, and contact electrodes (13) which form ohmic contacts with the detector layer (12). The invention also relates to a measurement device which is equipped with at least one such radiation detector (10).

17 Claims, 4 Drawing Sheets

(56) References Cited

U.S. PATENT DOCUMENTS

| | | | |
|---|---|---|---|
| 7,053,375 B2 | 5/2006 | Ando et al. | |
| 7,718,963 B2 | 5/2010 | Seefeldt et al. | |
| 7,796,174 B1 | 9/2010 | Harwit et al. | |
| 2002/0195568 A1* | 12/2002 | Mori et al. | 250/370.11 |
| 2003/0052701 A1 | 3/2003 | Brown et al. | |
| 2003/0107001 A1* | 6/2003 | Baumgartner et al. | 250/370.11 |
| 2003/0202630 A1* | 10/2003 | Chen | 378/62 |
| 2004/0113084 A1 | 6/2004 | Nakata et al. | |
| 2006/0018431 A1* | 1/2006 | Kanemitsu | 378/117 |
| 2008/0157253 A1 | 7/2008 | Starikov et al. | |
| 2008/0240360 A1* | 10/2008 | Jabri | 378/163 |
| 2009/0014659 A1* | 1/2009 | Hennessy et al. | 250/370.09 |
| 2010/0069749 A1 | 3/2010 | Lu et al. | |
| 2013/0009262 A1* | 1/2013 | Dowben | H01L 31/0321 257/428 |
| 2014/0112432 A1 | 4/2014 | Thalhammer et al. | |
| 2015/0041662 A1 | 2/2015 | Thalhammer et al. | |

FOREIGN PATENT DOCUMENTS

| | | |
|---|---|---|
| FR | 2911965 A1 | 8/2008 |
| FR | 2945128 A1 | 11/2010 |
| JP | 2010067738 A | 3/2010 |
| WO | 2010142273 A2 | 12/2010 |

OTHER PUBLICATIONS

Duboz et al., "GaN for x-ray detection", Applied Physics Letters, vol. 92, pp. 263501-1-263501-3 (2008).

Hofstetter et al., "Real-time x-ray response of biocompatible solution gate AlGaN/GaN high electron mobility transistor devices", Applied Physics Letters, vol. 96, pp. 092110-1-092110-3 (2010).

International Search Report for PCT/EP2012/000945 dated Nov. 6, 2012.

* cited by examiner

RADIATION DETECTOR AND MEASUREMENT DEVICE FOR DETECTING X-RAY RADIATION

BACKGROUND OF THE INVENTION

The invention relates to a radiation detector for detection of X-ray radiation, which is constructed with a GaN-based semiconductor material. Furthermore, the invention concerns a measuring device, which contains at least one such radiation detector, and applications of the radiation detector and of the measuring device.

It is known to use Gallium nitride (GaN) in semiconductor detectors for detection of X-ray radiation. For example, a GaN sensor is described in US 2010/0069749 A1, which emits luminescent light in response to a X-ray radiation. The luminescent light is conducted from the sensor via a light guide to a photodetector. This technique has disadvantages, since the combination of the sensor with the light guide represents a sensitive structure and since the detected X-ray radiation is not directly converted in an electric measurement signal.

Furthermore, in "Applied Physics Letters" Vol. 92, 2008, pp. 263501, J.-Y. Duboz et al. analyze the suitability of GaN for detection of X-ray radiation. For this purpose, GaN layers, e.g. with a thickness of 110 µm or 480 µm, were deposited on silicon or sapphire substrates and provided with contact electrodes, which formed a Schottky contact with the GaN layer. It was, however, found that a reliable detection was limited to X-ray radiation with an energy value below 20 keV. For practical applications of a radiation detector, for example in dosimetry, a sensitivity to X-ray radiation with an energy value above 20 keV is, however, required.

Finally, M. Hofstetter et al. describe in "Applied Physics Letters" Vol. 96, 2010, pp. 092110, a radiation detector for X-ray radiation, which contains a so-called HEMT ("high electron mobility transistor") with a GaN-based multi-layer system. This radiation detector can likewise have disadvantages due to its multi-layer structure.

In practice, it has shown that the hitherto described GaN-based radiation detectors are not suitable, in particular due to their complex structure, a complex calibration and/or an insufficient sensitivity for routine application in dosimetry. Furthermore, no practical applications of GaN-based radiation detectors, for example in medical engineering, the material testing or radiation monitoring were hitherto described.

The objective of the invention is to provide an improved radiation detector by means of which the disadvantages of conventional radiation detectors are overcome. The radiation detector should be characterized in particular by a simplified structure, simplified operation and/or an increased sensitivity compared with conventional detectors. The objective of the invention is furthermore to provide measuring devices and applications of the radiation detector by means of which disadvantages of conventional techniques for detection of X-ray radiation are overcome.

These objectives are achieved by a radiation detector of the invention and by a measuring device of the invention, which contains at least one such radiation detector.

DESCRIPTION OF THE INVENTION

According to a first general aspect of the invention, a radiation detector is provided for detection of X-ray radiation, which comprises a carrier substrate, a GaN-based detector layer arranged on the carrier substrate and contact electrodes connected with the detector layer. According to the invention, the detector layer has a thickness, which is less than 50 µm. It is furthermore provided for according to the invention that the contact electrodes form ohmic contacts with the detector layer. The inventors have found that one single detector layer provided with ohmic contacts and having said considerably reduced layer thickness compared with conventional radiation detectors allows a sensitive, reproducible and a detection of X-ray radiation, which only requires a simple resistance or conductivity measurement. When applying a voltage on the detector layer with the contacts, a current measurement provides a resistance or conductivity value. The detector layer acts like a photoconductor, in which a photo-current is generated in response to X-ray radiation, which photo-current can be measured at the contact electrodes. The detected X-ray radiation is thus directly converted into an electrical measurement signal (detector current, resistance or conductivity value). The conversion yield is in this process great to such an extent that the radiation detector according to the invention can be miniaturized and can be adapted for numerous applications in dosimetry. Preferably, the radiation detector is designed for detection of X-ray radiation in an energy range of 1 keV to 300 keV, in particular above 50 keV.

Advantageously, the radiation detector according to the invention represents a beam sensor, which uses the photoconductive properties of wide band gap semiconductors. Under the effect of radiation, the conductive detector volume changes. Physically, no predefined electric barrier layer is in this process required as is the case for conventional semiconductor detectors. This allows a novel detection mode for the dosimetry. The detection of the radiation is based upon the principle of a photoconductor with internal amplification properties. No electric barrier layer is required but, rather, a volume-independent measurement by means of the ohmic contacts is provided for. The measurement signal can be represented in different ways (e.g. electronic, graphical, acoustic).

The functional principle of the GaN radiation detector according to the invention fundamentally differs from the conventionally available semiconductor detectors for X-ray radiation, for which photo-induced charge carriers are collected by means of an electric field. In contrast, a radiation-induced change in the resistance takes place at the GaN sensors (photoconductor), by changing the detector volume where the charge transfer takes place. Although space-charge zones also occur in the GaN sensors (first and foremost through surface effects), the electric current passes through the semiconductor parallel to these space-charge zones. The irradiation leads to imbalance of free charge carrier concentrations, which change the total volume of the space-charge zones and thus the volume, which contributes to the charge transport. This results in the fact that the height of the measurement signal is not directly limited to the generation of free charge carriers, but rather a massive internal amplification can take place, whereby increased detection sensitivities compared with conventional techniques are possible.

According to a second general aspect of the invention, a measuring device is provided, which is equipped with at least one radiation detector according to the first aspect of the invention. The measuring device is generally an examination device, which is adapted for dosimetry and optionally for further functions, such as a cultivation of biological cells. Due to the miniaturizability of the radiation detector according to the invention, the measuring device is suitable in particular for spatially resolved dosimetry.

According to a preferred embodiment of the invention, the thickness of the detector layer is less than 10 µm, in particular less than 5 µm. Preferably, the thickness of the detector layer is greater than 100 nm, in particular greater than 500 nm. The low thickness of the GaN-based detector layer offers advantages both with respect to the manufacture of the radiation detector and also with respect to its integration in the measuring device. According to further preferred embodiments of the invention, the detector layer has a surface, which is less than 100 mm$^2$, in particular less than 10 mm$^2$. The surface is preferably greater than 1 µm, in particular greater than 0.1 mm$^2$.

Preferably, the radiation detector comprises a single detector layer. In other words, exclusively one layer is provided for, which is fitted with ohmic contacts and is provided for generation of the measurement signal. Particularly preferably, the detector layer consists of GaN, which can optionally contain a doping, for example of iron or carbon.

Further advantages for the miniaturization of the radiation detector result when the contact electrodes consist of two contact electrodes, which are arranged on one side, that is to say in particular on the side of the detector layer opposite the carrier substrate. The contacts are located jointly on the same surface of the detector layer.

Advantageously, the radiation detector can be provided with at least one of the following features in order to targetedly adapt the radiation detector for a specific application. According to a first variant, the radiation detector can have an encapsulation. The encapsulation comprises a sheath, for example made of plastic, which encloses the carrier substrate and the detector layer partially or on all sides. The radiation detector with the encapsulation forms an autarkic component with wireless signal transmission. Alternatively, for line-connected operation, merely connection lines for connection of the contact electrodes protrude into the environment of the encapsulation. Advantageously, the radiation detector with the encapsulation can be formed with a thickness of less than 10 mm, in particular 1 mm, which offers particular advantages for medical dosimetry. Particularly preferably, the encapsulation is liquid-tight, resistant against acids, resistant against bases, temperature-proof and/or pressure-resistant. This advantageously allows the application of the radiation detector in extreme environmental conditions, for example for dosimetry in a chemical reactor.

According to a further variant, the radiation detector can be provided with at least one adhesive surface. Providing the adhesive surface means that the radiation detector and/or, optionally, the encapsulation of the radiation detector is formed on at least one surface with an inherent tackiness. The adhesive surface has, for example, an adhesive agent, which allows sticking of the radiation detector to an object, for example on the surface of an object to be analyzed or of a subject.

According to a further variant, the radiation detector can be equipped with an electronic circuit, which is, for example, connected with the carrier substrate connected or optionally enclosed in the encapsulation. The electronic circuit can be adapted for current measurement, data storage and/or data transmission. The current measurement means that the electronic circuit can be used to detect an electrical measurement signal, which is characteristic for the photo-current generated in the detector layer in response to X-ray radiation. If the electronic circuit according to a particularly preferred variant of the invention is configured for wireless communication with an external control device and comprises for this purpose in particular a RFID device, this proves advantageous for the application of the radiation detector in complex structured objects to be analyzed.

According to a further variant of the invention, the radiation detector can be designed for an energy-resolved measurement of the X-ray radiation. For X-ray radiation with a dose rate above e.g. approx. 0.2 mGy/s, the detector works in an almost energy-independent manner. If monochromatic X-ray radiation with a known dose rate hits the detector, the energy of the radiation can thus be determined.

According to a further variant of the invention, the radiation detector can be equipped with a bendable material web. The carrier substrate can be connected with the material web, which comprises, for example, a planar or strip-shaped single-layered or multi-layered textile material. The use of the material web simplifies the fixing of the radiation detector on an object to be analyzed. Particularly preferably, the adhesive surface is provided for on the bendable material web. In this case, the carrier substrate with the detector layer is arranged on an adhesive tape, which can be fixed like a dressing plaster on a subject or accordingly on any other object to be analyzed. The adhesive tape can carry a plurality of radiation detectors, so that a detector array is created.

Advantageously, the encapsulation of the radiation detector can have a biocompatible surface. The encapsulation can consist of a biocompatible material, for example PDMS, PEN, PET, plastic, or photoresist, or bear a coating made of the biocompatible material. Advantageously, impairment of a biological object to be analyzed, in particular during implantation of the radiation detector in an organism, is thus avoided.

According to preferred variants of the invention, the radiation detector is part of an endoscopic device, part of an adhesive tape, part of a cultivation device for biological cells and/or part of an implant device, which is configured for implantation in or on a living organism. Due to the miniaturizability of the radiation detector, the latter can unproblematically be arranged in an endoscopic device, which would be used to carry out dosimetric measurements inside an organism or another object to be analyzed. The integration of the radiation detector in a cultivation device for biological cells, such as a cell incubator or a fluidic microsystem, which is adapted for handling biological cells, advantageously allows that dosimetric measurements can be carried out in real time under the concrete cultivation conditions.

According to a preferred embodiment of the measuring device according to the invention, it is equipped with a housing, in which the at least one radiation detector is movable. This advantageously simplifies the application of the measuring device as a material testing device.

According to a further preferred variant of the invention, the measuring device is equipped with a plurality of radiation detectors, which are arranged along a predetermined reference line or reference surface. The radiation detectors can, for example, form a line array along a straight or curved line or a surface array along an plane or curved reference surface. These variants of the invention are particularly advantageous for imaging dosimetry using the radiation detector according to the invention.

Further preferred features of the measuring device according to the invention comprise an alarm device, a positioning device and/or a transducer device. The alarm device is configured to generate an alarm, for example an optical or acoustic alarm, when undesirable radiation dose values are exceeded. Advantageously, the measuring device according to the invention can in this case represent a radiation indicator, which is operated like a conventional smoke detector. The positioning device can be adapted for positioning the at least one radiation detector relative to an object to be analyzed. The positioning device can for example be provided for in the housing of the measuring device. This advantageously allows spatially resolved dosimetric measurements on the object to be analyzed. Finally, the transducer device allows the measurement of time series of dosage values, for example for monitoring of an object to be analyzed, such as a room or a carrier of the radiation detector.

In summary, the radiation detector according to the invention has the following advantages. The radiation detector can be manufactured by lithographic processes and can therefore be easily miniaturized. The detector size (in particular extension of the sensitive surface) is almost unrestrictedly scalable, in particular in the range of several hundreds μm up to 1 μm, preferred in the size of 30 μm. Operation in liquids, in particular acids and bases, is possible. Combined potential measurements with HEMT are possible, whereby multi-parameter measurements of ion changes in e.g. cell media are possible. The radiation detector according to the invention does not require additional in situ electronics and can be operated spatially independent of a control electronic system. Furthermore, cooling of the radiation detector is not necessary. The radiation detector according to the invention has a very low angle-dependency of the detector signal from incident radiation, so that a universal installation is possible.

Furthermore, the radiation detector according to the invention has a very wide power measurement range, a very large dose rate measurement range and almost no energy-dependency in the diagnostic X-ray range. Due to the extremely wide detection ranges of the GaN sensors (energy and dose rate), the option of biocompatibilization and the option of miniaturization, the GaN sensors offer a considerable potential in the area of medicine as well as in medical-technical applications. Finally, the radiation detector allows a 3-dimensional dosimetry with the option of imaging.

The following advantages results, in particular, from application in the diagnostics with MRT-PET combinations. A problem with conventional PET scanners is the missing compatibility of high magnetic fields and photomultipliers, which hitherto serve as detectors in combination with scintillators. The advantage of the invention lies in the fact that a detector is provided, which is insensitive to high fields, so that a "one-stop shop" MRT-PET scanner can be constructed. The invention furthermore allows the integration of gamma detectors (PET/SPECT detectors) in MRT scanners for simultaneous, functional and morphological extraction of information, shortening of the examination time, a "one-stop shop" examination, and, because the detector and the electronic system can be placed separately, reduction of the detector size.

BRIEF DESCRIPTION OF THE DRAWINGS

Further details and advantages of the invention will be explained below with reference to the preferred embodiments of the invention represented in the attached drawings. The figures show as follows.

Figure 1:
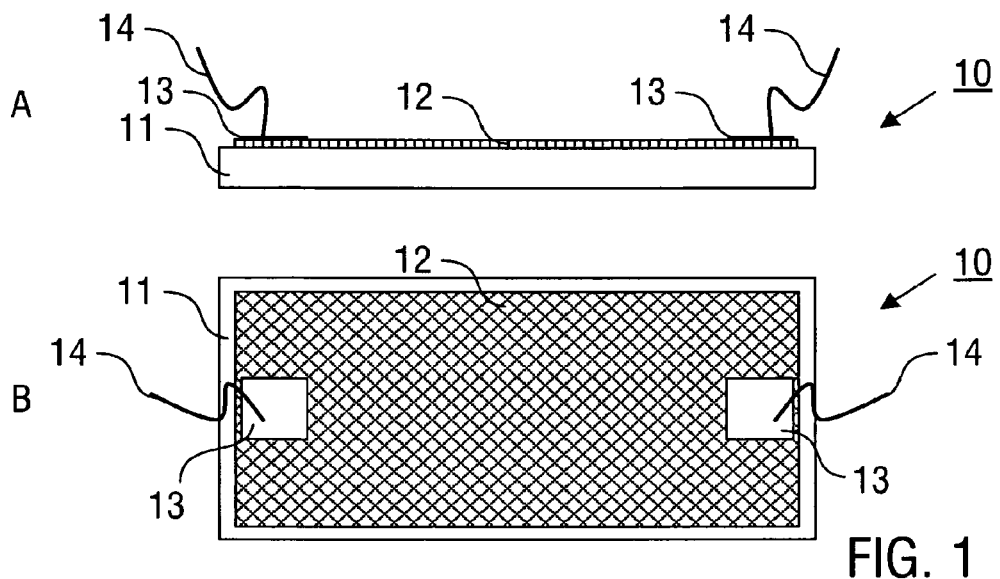
FIGS. 1A and 1B: a schematic sectional view and a schematic top view onto a first embodiment of a radiation detector according to the invention.

According to FIGS. 1A and 1B, the radiation detector 10 comprises a carrier substrate 11, a detector layer 12 and contact electrodes 13, which can be connected by means of connection lines 14 with an electronic circuit for current measurement (not represented). The carrier substrate 11 comprises, for example, sapphire with a thickness of 0.33 mm. The detector layer 12 consists of GaN with a thickness of, for example, 2.5 μm. The contact electrodes 13 consist, for example, of Ti/Al. They are applied by means of thermal vapour deposition or electron beam vapour deposition on the GaN detector layer 12, so that an ohmic contact is formed between the contact electrodes 13 and the detector layer 12, respectively, after thermal heating-out (annealing). The dimensions of the detector layer 12 (FIG. 1B) are for example 0.5 mm·2 mm, whereas the dimensions of the contact electrodes 13 are, for example, 300 μm·300 μm, respectively. The radiation detector 10 is sensitive to X-ray radiation with an energy of 20 to 300 keV up to values in the μGy range.

Figure 2:
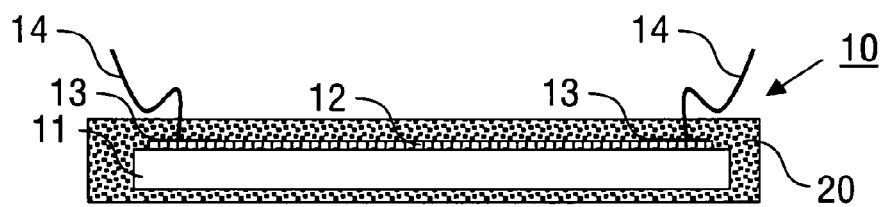
FIGS. 2 to 5: schematic illustrations of further embodiments of the radiation detector according to the invention.

FIG. 2 illustrates an embodiment of the invention, in which the radiation detector 10 is equipped with an encapsulation 20. The carrier substrate 11 and the detector layer 12 as well as the contact electrodes 13 are fully enclosed by the encapsulation 20. According to a modified variant of the invention, a partial encapsulation can be provided for. For example, during uses of the radiation detector, it can be advantageous if only the electric contacts are encapsulated and the remaining sensitive surface between the contact is not encapsulated. The encapsulation 20 consists, for example, of epoxy resin. It has, for example, a thickness of 0.5 mm. If the application of the radiation detector 10 on the surface or inside a biological organism is provided for, the encapsulation 20 has on all sides a biocompatible surface, for example consisting of PDMS.

Figure 3:
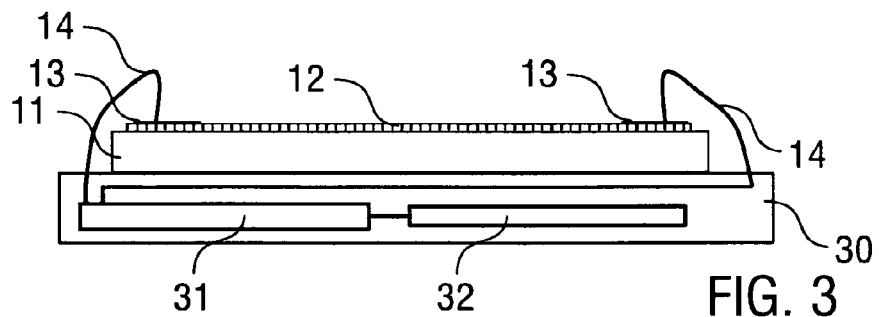

FIG. 3 illustrates an embodiment of the radiation detector 10, in which the carrier substrate 11 is connected with an electronic circuit 30. The connection lines 14 of the contact electrodes 13 directly lead into the electronic circuit 30, which comprises in the represented example at least one circuit 31 and an antenna 32. The circuit 31 is adapted for measurement of the photo-current generated in the detector layer 12 in response to X-ray radiation and for storage of measured values, which represent the photo-current or values derived therefrom. The circuit 31 can also be provided for as a transducer device by means of which dosage values can be repeatedly recorded in the temporal course (time resolved monitoring). The antenna 32 is configured for wireless communication with an external control device (not represented). The electronic circuit comprises, for example, a RFID chip.

Figure 4:
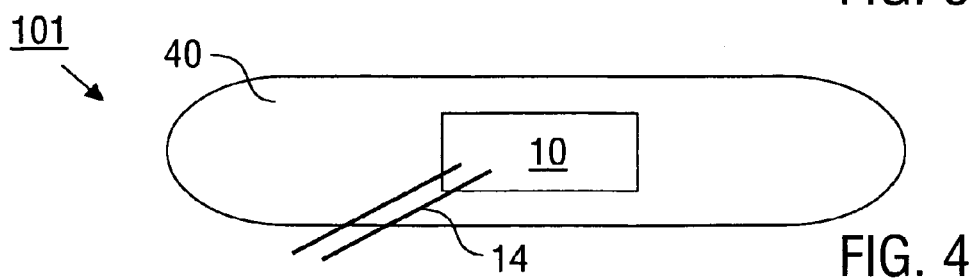

FIG. 4 illustrates a measuring device 101 with an adhesive tape 40 on the surface of which the schematically shown radiation detector 10 is arranged. The radiation detector 10 is connected wirelessly or, as represented, via connection lines 14 with a control device (not represented), which is provided for recording of measured values from the radiation detector 10. The compound made up of the adhesive tape 40 and the radiation detector 10 represents a measuring device, which can be fixed on the surface of the object to be analyzed, for example of a patient, like a "plaster". This advantageously allows a spatially resolved dosimetry on the surface of the patient, for example in the course of a radiation treatment.

For this embodiment of the invention, the radiation detector is preferably designed for wireless communication with the external control device. The adhesive tape 40 preferably consists of a fabric tape or a textile tape with an adhesive layer, as is known per se from conventional dressing materials.

Figure 5:
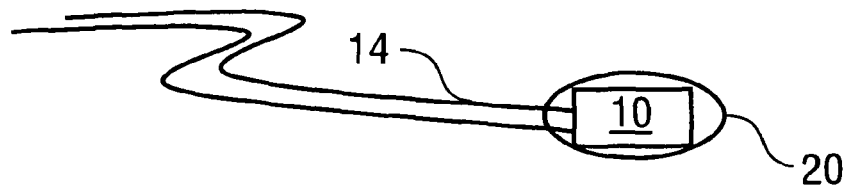
Figure 6:
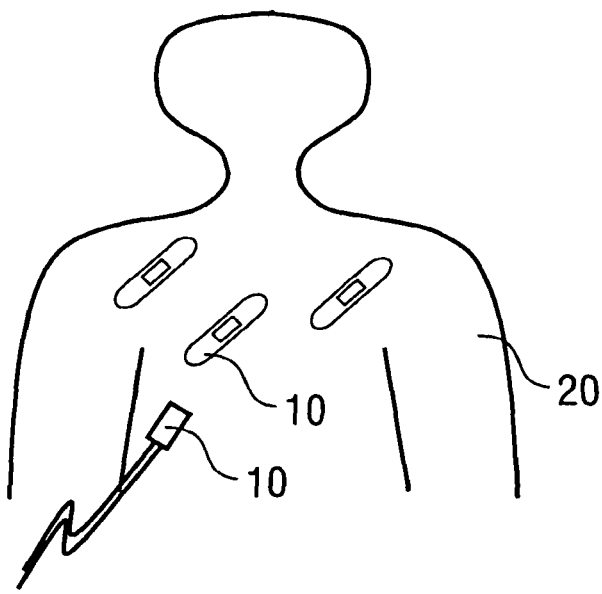
FIG. 6: a schematic illustration of the positioning of the radiation detector according to the invention on the body of a subject.

FIG. 5 illustrates schematically the encapsulated radiation detector 10 with connection lines 14, which may be conducted in a single cable out of the encapsulation 20. FIG. 6 illustrates schematically the positioning of radiation detectors 10 according to FIG. 4 or 5 on the skin surface of a subject. Alternatively, a subcutaneous arrangement or an arrangement in a cavity of the subject body is possible.

Figure 7:
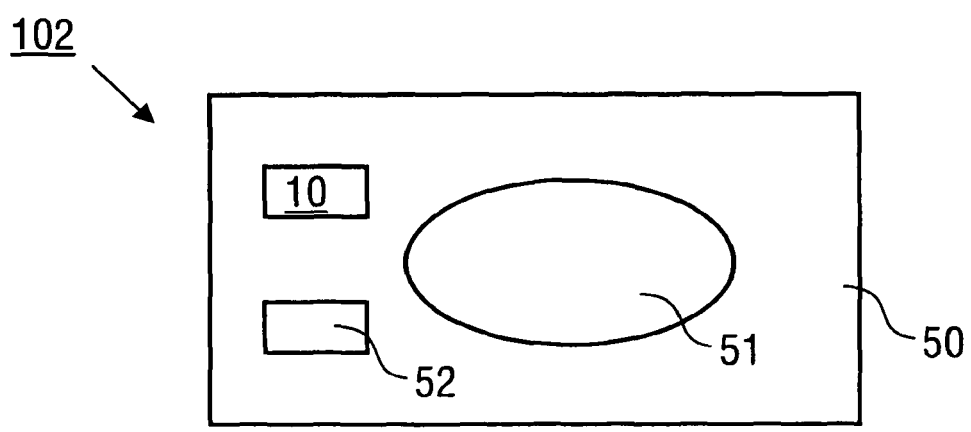
FIGS. 7 to 9: preferred embodiments of measuring devices according to the invention, which contain at least one radiation detector.

FIG. 7 illustrates the radiation detector according to the invention as part of an endoscopic device, which is part of a cultivation device 102 for biological cells. The cultivation device 102 comprises e.g. a plate 50, in or on which a cultivation substrate 51, e.g. shaped as a dish, the radiation detector 10 and a sensor device 52 are arranged for detection of cultivation conditions. The cultivation device 102 can for example be constructed as a fluidic microsystem.

Figure 8:
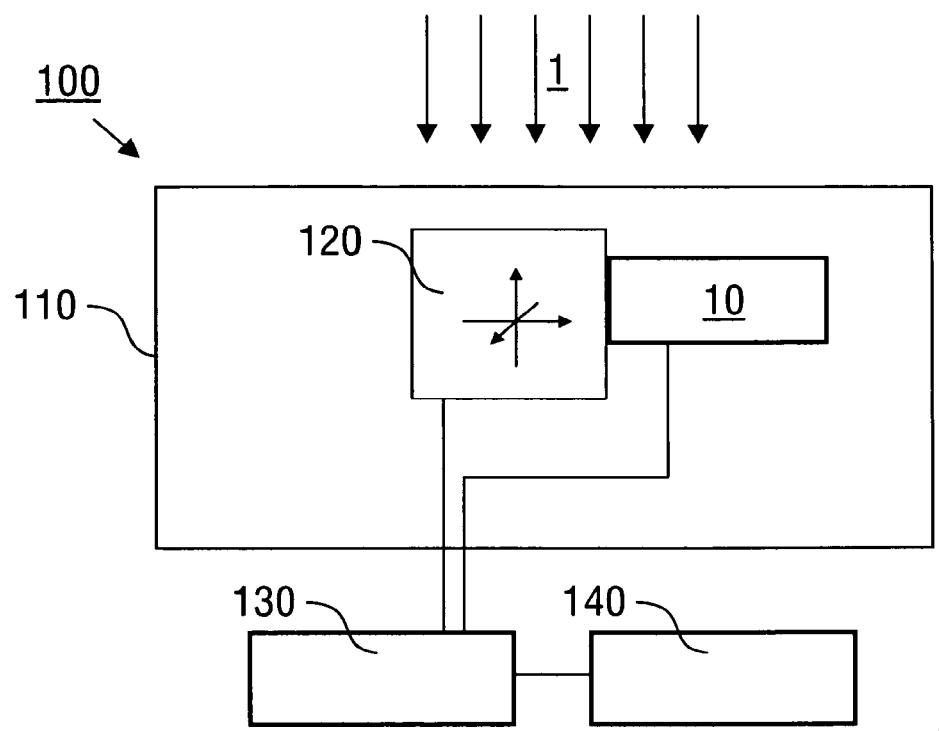

FIG. 8 illustrates schematically a further embodiment of a measuring device 100 according to the invention, which is adapted, for example, for dosimetry during material testing. The measuring device 100 comprises a housing 110, in which at least one radiation detector 10 is movably arranged. For positioning of the radiation detector 10 in the housing 110, a positioning device 120 is provided for, which comprises, for example, a setting device for moving the radiation detector 10 in all three spatial directions. The positioning device 120 and the radiation detector are connected with a control device 130, which firstly serves for controlling the positioning device 120 and secondly for recording the measured values delivered by the radiation detector 10. The control device 130 can be connected with an output device 140, such as a display device and/or a printer. The control device 130 and the output device 140 can be realized by a computer, optionally with additional devices.

When positioning the measuring device 100 in the radiation field of X-ray radiation 1, the radiation detector 10 can be moved in the radiation field in order to, for example, record a radiation profile.

Figure 9:
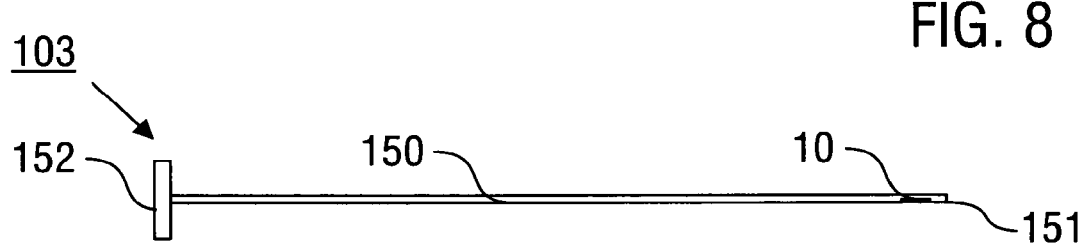

For medical applications, an embodiment of the measuring device is of particular interest, this being an endoscopic device 103, as is schematically illustrated in FIG. 9. The endoscopic device 103 comprises a rigid or flexible endoscope shaft 150 with a free end 151, which is provided for insertion into an object to be analyzed, for example in the interior of a subject, and with a coupling device 152 provided on the opposite end for connection of the endoscopic device 102 with a medical examination apparatus. The radiation detector 10 is fixed close to the free end 151 or movable in the longitudinal direction of the endoscope shaft 150. Furthermore, the radiation detector 10 is connected through connection lines, which run through the endoscope shaft 150, with a control device. In the last case, radiation profiles can be recorded in the object to be analyzed without having to move the endoscope. The endoscopic device 102 is used as is known per se for conventional endoscopes, wherein, according to the invention, a novel functionality of the endoscopic device 103 is achieved by providing the radiation detector 10 in the endoscope shaft.

Figure 10:
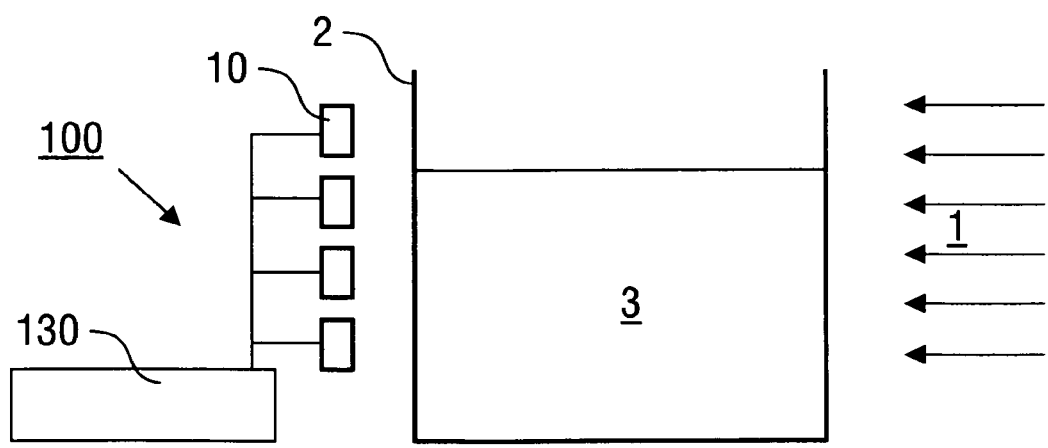
FIGS. 10 to 12: schematic illustrations of further preferred applications of the measuring device.

A measuring device according to the invention 100 can be equipped with a plurality of radiation detectors 10, as is schematically illustrated in FIG. 10. For example, four radiation detectors 10 are provided for, which form a detector array and are connected with a control device 130. The object to be analyzed represents, for example, a container 2, in which a liquid 3 is contained. In the case of irradiation of the container 2 with X-rays 1, the fill level in the container 2 can be determined through reading from the radiation detectors 10.

Figure 11:
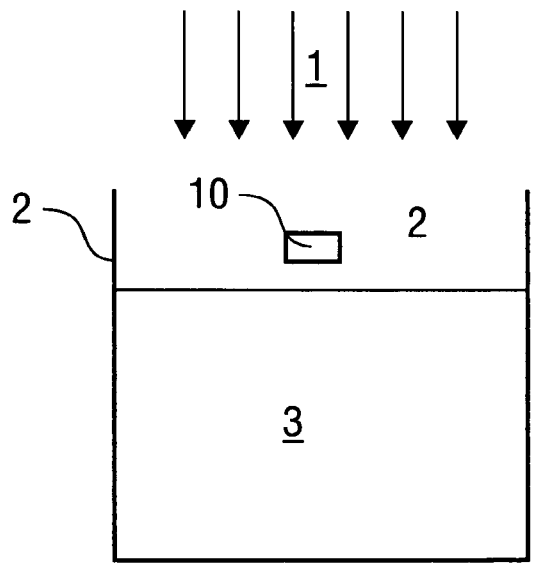

A further application of the radiation detector for scattered radiation measurement in proximity to an object to be analyzed is illustrated schematically in FIG. 11. In this case, the object to be analyzed is likewise illustrated by a container 2 with a liquid 3, whose surface is to be examined with respect to the back-scattering of X-ray radiation 1. The radiation detector 10 can be moved in the container 2 over the surface of the object to be analyzed, in particular over the surface of the liquid 3, wherein a high spatial resolution can be achieved due to the small internal volume.

Figure 12:
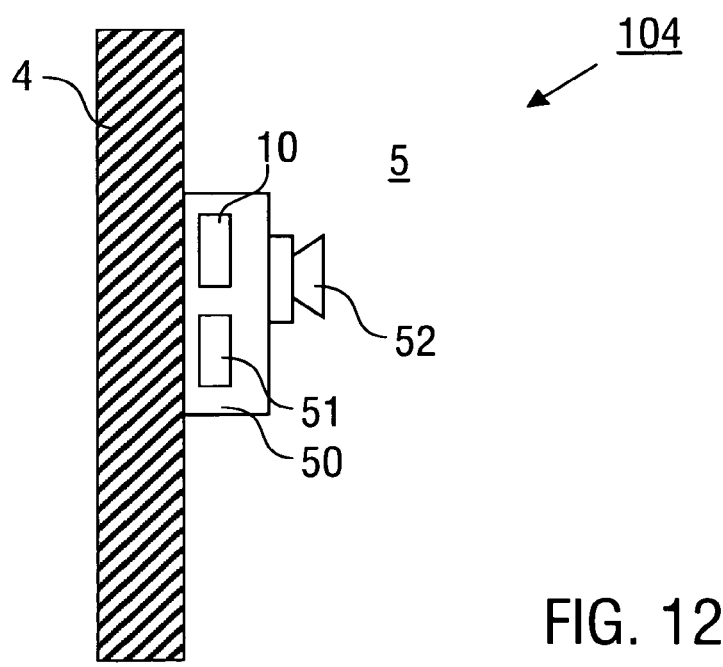

Finally, FIG. 12 illustrates the use of the measuring device according to the invention as a radiation indicator 104. The radiation detector 10 is arranged jointly with an electronic circuit 61 in a common housing 60, which is furthermore equipped with an alarm device 62, for example a sound transmitter. The radiation indicator 104 is, for example, fixed on a wall 4, which delimits a room 5 to be monitored dosimetrically. If the radiation dose in the room is exceeded, the sound transmitter 62 emits an alarm signal. The embodiment according to FIG. 9 is particularly advantageously suitable for application as environmental sensor for background radiation or as sensor in radiation systems with energy resolution.

The features of the invention disclosed in the preceding description, the drawings and the claims can both individually and in combination be of significance for the realization of the invention in its different embodiments.

The invention claimed is:

1. A radiation detector for detection of X-ray radiation, comprising:
   a carrier substrate,
   a photoconductor detector layer, which contains GaN, is arranged on the carrier substrate and has a thickness of less than 50 µm, said detector layer having a lower surface connected with the carrier substrate and an upper surface opposite to the carrier substrate, and
   contact electrodes, which form ohmic contacts with the detector layer, wherein
   the contact electrodes comprise electrode pads arranged at opposite edges of the upper surface of the detector layer, and
   the upper surface of the detector layer substantially is directly exposed to the surroundings.

2. The radiation detector according to claim 1, comprising at least one of the features:
   the thickness of the detector layer is less than 10 µm,
   the detector layer has a surface, which is less than 100 mm$^2$,
   the contact electrodes comprise two contact electrodes, and
   the GaN is doped with Fe or C.

3. The radiation detector according to claim 1, comprising at least one of the features:
   the thickness of the detector layer is less than 5 µm, and
   the detector layer has a surface, which is less than 10 mm$^2$.

4. The radiation detector according to claim 1, comprising at least one of the features:
   the radiation detector has an encapsulation,
   the radiation detector is provided with an adhesive surface,
   the radiation detector has an electronic circuit, which is adapted for at least one of current measurement, data storage and data transmission, and
   the radiation detector is designed for an energy-resolved measurement.

5. The radiation detector according to claim 4, wherein the encapsulation is at least one of liquid-tight, resistant against acids, resistant against bases, temperature-proof and pressure-resistant.

6. The radiation detector according to claim 4, wherein the electronic circuit has a RFID device.

7. The radiation detector according to claim 4, wherein the adhesive surface is formed on a bendable material web by means of which the carrier substrate is connected.

8. The radiation detector according to claim 4, wherein the encapsulation has a biocompatible surface.

9. The radiation detector according to claim 1, which is part of at least one of
an endoscopic device,
an adhesive tape,
a cultivation device for biological cells, and
an implant device, which is configured for implantation in or on a living organism.

10. A measuring device, which is provided with at least one radiation detector according to claim 1.

11. The measuring device according to claim 10, wherein a housing is provided for, in which the at least one radiation detector is movable.

12. The measuring device according to claim 10, which is a cultivation device for biological cells or an endoscopic device.

13. The measuring device according to claim 10, wherein a plurality of radiation detectors are provided for, which are arranged along a reference line or a reference surface.

14. The measuring device according to claim 10, which is provided with at least one of
an alarm device,
a positioning device, which is configured for positioning the at least one radiation detector relative to an object to be analyzed, and
a transducer device, which is configured for repeated recording of dosage values depending on time.

15. A method of using a measuring device according to claim 10, said method comprising:
providing the measuring device; and
conducting dosimetry of X-ray radiation.

16. A method of using a radiation detector according to claim 10, said method comprising:
providing the radiation detector; and
conducting dosimetry of X-ray radiation to detect radiation.

17. The radiation detector of claim 1, wherein said radiation detector is without any contact electrodes on said carrier substrate.

* * * * *